US011667906B2

(12) United States Patent
Caracci et al.

(10) Patent No.: US 11,667,906 B2
(45) Date of Patent: Jun. 6, 2023

(54) MAGNETIC MICROCARRIERS

(71) Applicant: Corning Incorporated, Corning, NY (US)

(72) Inventors: Stephen Joseph Caracci, Elmira, NY (US); Ye Fang, Painted Post, NY (US); Ann MeeJin Ferrie, Painted Post, NY (US); Yan Jin, Sunnyvale, CA (US); Lingyan Wang, Horseheads, NY (US); Yue Zhou, Horseheads, NY (US)

(73) Assignee: CORNING INCORPORATED, Corning, NY (US)

( * ) Notice: Subject to any disclaimer, the term of this patent is extended or adjusted under 35 U.S.C. 154(b) by 303 days.

(21) Appl. No.: 14/950,771

(22) Filed: Nov. 24, 2015

(65) Prior Publication Data

US 2016/0145600 A1    May 26, 2016

Related U.S. Application Data

(60) Provisional application No. 62/083,493, filed on Nov. 24, 2014.

(51) Int. Cl.
*C12N 13/00* (2006.01)
*C12N 1/02* (2006.01)
*H01F 1/37* (2006.01)
*H01F 1/26* (2006.01)

(52) U.S. Cl.
CPC ............... *C12N 13/00* (2013.01); *C12N 1/02* (2013.01); *H01F 1/26* (2013.01); *H01F 1/37* (2013.01)

(58) Field of Classification Search
CPC .............. C12N 13/00; C12N 1/02; H01F 1/26
See application file for complete search history.

(56) References Cited

U.S. PATENT DOCUMENTS

| | | | | |
|---|---|---|---|---|
| 4,654,267 | A * | 3/1987 | Ugelstad | B03C 1/01 428/407 |
| 4,994,388 | A | 2/1991 | Hillegas et al. | |
| 7,818,980 | B2 | 10/2010 | Burdette et al. | |
| 2005/0054101 | A1 | 3/2005 | Felder et al. | |
| 2006/0260777 | A1* | 11/2006 | Rashba-Step | A61K 9/0019 162/181.1 |
| 2007/0212540 | A1* | 9/2007 | Cheng | B01J 20/262 428/402 |
| 2010/0081215 | A1 | 4/2010 | De Geest et al. | |
| 2010/0297019 | A1* | 11/2010 | Lanza | A61K 49/0002 424/9.2 |
| 2010/0301257 | A1* | 12/2010 | Modahl | C08F 2/22 252/62.54 |
| 2012/0143039 | A1* | 6/2012 | Hartwig | A61K 9/0009 600/409 |

FOREIGN PATENT DOCUMENTS

| | | |
|---|---|---|
| CN | 102660510 A | 9/2012 |
| EP | 1903337 B1 | 3/2008 |
| IN | 2006DN370 A | 8/2007 |
| IN | 201108203 P1 | 1/2013 |

OTHER PUBLICATIONS

Jiang et al. "Superparamagnetic core-shell structured microspheres carrying carboxyl groups as adsorbents for purification of genomic DNA." Colloids and Surfaces A: Physicochem. Eng. Aspects 401 (2012) 74-80.*
Namanga et al "Synthesis and Magnetic Properties of a Superparamagnetic Nanocomposite Pectin-Magnetite Nanocomposite" Journal of Nanomaterials vol. 2013, Article ID 137275, p. 1-8 http://dx.doi.org/10.1155/2013/137275.*
Taylor et al. "The Microbial Metabolism of Acetone" Journal of General Microbiology, 118, 159-170.*
Zhang et al. Water Research 42 (2008 ) 2204-2212.*
Cai et al. Preparation of composite magnetic microspheres by reactive blending; Chinese Journal of Polymer Science vol. 29, No. 5, 2011, 580-585 (Year: 2011).*
Cao et al., Preparation and characterization of magnetic microspheres for the purification of interferon α-2b, Journal of Chromatography B, 833 (2006) 236-244 (Year: 2006).*
Skowronski, E. et al., "Magnetic, Microplate-format Plasmid Isolation Protocol for High-Yield, sequencing-grade DNA." BioTechniques, vol. 29, pp. 786-792, Oct. 2000.
Beheke, C. et al., "Polymeric Plant-derived Excipients in Drug Delivery." Molecules, vol. 14, pp. 2602-2620, Jul. 16, 2009.
Global Cell Solutions, "GEM: 3-D Cell Culture Simplified." Datasheet, 4 pages, 2009.
"Co-encapsulation of magnetic nanoparticles and doxorubicin into biodegradable microcarriers for deep tissue targeting by vasular MRI navigation". Biomaterials, vol. 32, Issue 13, May 2011, pp. 3481-3486.
"Encapsulation and release of plasminogen activator from biodegradable magnetic microcarriers", European Journal of Pharmaceutical Sciences, vol. 35, Issues 1-2, Sep. 2, 2008, pp. 96-103.

* cited by examiner

*Primary Examiner* — Robert J Yamasaki
(74) *Attorney, Agent, or Firm* — Michael G. Panian

(57) ABSTRACT

Magnetic microcarrier beads have a particle size of 1 to 1000 micrometers and include a composite core and a polymer coating that surrounds and encapsulates the core. The composite core includes magnetic particles embedded within an indigestible polymer matrix. The coating is a digestible or indigestible polymer that facilitates cell adhesion to the surface of the beads during cell culture. Magnetic force can be used to agitate the microcarrier beads during cell culture as well as to separate the beads from cultured cells or processed bio-media.

18 Claims, 2 Drawing Sheets

MAGNETIC MICROCARRIERS

This application claims the benefit of priority under 35 U.S.C. § 119 of U.S. Provisional Application Ser. No. 62/083,493 filed on Nov. 24, 2014 the content of which is relied upon and incorporated herein by reference in its entirety.

BACKGROUND

1. Field

The present disclosure relates generally to methods of making magnetic microcarriers, and more specifically to surface-modified magnetic microcarriers that may be used, by way of example, for the isolation of proteins, cells, and viruses and also for diagnostic applications and cell cultivation.

2. Technical Background

In contrast to cell culture on flat surfaces where adhesive cells can reach high confluence and thus limit cell expansion via cell-to-cell contact inhibition, spherical microcarriers having a high ratio of surface area/volume present an attractive platform for efficient cell culture scale-up or expansion where either harvested cells or conditioned media can be the desired product.

Incumbent to cell culture is adequate oxygenation and supply of nutrients to the cells. An associated challenge includes stirring of the microcarriers to provide the required oxygen and nutrients without introducing hydrodynamic stresses sufficient to damage the growing cells. Conventionally the stirring is done using impellers, though this approach involves the expense of cleaning and sterilizing the hardware, as well as the generation of mechanical shear forces that may damage the cultured cells.

A further challenge involves separating the microcarriers from the cells or conditioned media. Enzymatic treatment may be used to harvest adhesive cells, for example, though the addition of enzymes can damage the cells. Proteolytic enzymes, for example, may non-selectively clear cell surface receptors.

Magnetic particles or beads are used within the biotechnology field in a range of applications including cell culture, extraction and purification of nucleic acids and proteins as well as viruses and whole cells. During use, target biomacromolecules (e.g., DNA, proteins) bind to the surface of the particles, whereupon they can be manipulated magnetically.

It would be advantageous to provide a low-cost, efficient approach to synthesize magnetic particles having, for example, a controlled particle size, composition, uniformity and crystalline structure, as well as a surface chemistry supportive of cell attachment and/or growth.

BRIEF SUMMARY

In accordance with embodiments of the present disclosure, surface-modified magnetic beads enable cell attachment, expansion and/or cell separation or purification and can be used to culture a variety of cell types, including transformed, primary and stem cells. Such beads, which can be used in conjunction with a variety of cell-based assays, can be stirred using a magnetic field. Various surface modifications can enhance cell attachment, improve cell growth, and enable self-digestible and enzyme-free cell release. Cells can grow and expand on the surface of the microcarriers using serum, serum-free media, or chemically-defined media.

In the case of harvesting cells, the surface of the microcarriers can be dissolved or digested such that the cultured cells can be harvested without using any protease. In the case of harvesting conditioned media, the microcarriers can be separated from the media using magnetic force. Before or after the cell harvest, microcarriers can be separated from the culture media or liquid phase using a magnetic field.

In one embodiment, a magnetic bead comprises a composite core and a coating that surrounds and encapsulates the core. The composite core comprises magnetic particles embedded within an indigestible polymer matrix and the coating comprises a digestible or indigestible polymer.

A method for preparing conditioned media comprises culturing cells on the surface of the microcarrier beads to form conditioned media and separating the conditioned media from the magnetic bead using magnetic force. A method for harvesting cultured cells comprises culturing cells on the surface of the microcarrier beads, disassociating the cells from the surface, and separating the dissociated cells from the magnetic beads using magnetic force. The disassociating can be accomplished free of a protease. The disassociating can also be accomplished using a mixture of non-proteolytic enzyme and a proteolytic enzyme, in particular when individual or isolated cells are desired end products.

Additional features and advantages of the subject matter of the present disclosure will be set forth in the detailed description which follows, and in part will be readily apparent to those skilled in the art from that description or recognized by practicing the subject matter of the present disclosure as described herein, including the detailed description which follows, the claims, as well as the appended drawings.

It is to be understood that both the foregoing general description and the following detailed description present embodiments of the subject matter of the present disclosure, and are intended to provide an overview or framework for understanding the nature and character of the subject matter of the present disclosure as it is claimed. The accompanying drawings are included to provide a further understanding of the subject matter of the present disclosure, and are incorporated into and constitute a part of this specification. The drawings illustrate various embodiments of the subject matter of the present disclosure and together with the description serve to explain the principles and operations of the subject matter of the present disclosure. Additionally, the drawings and descriptions are meant to be merely illustrative, and are not intended to limit the scope of the claims in any manner.

BRIEF DESCRIPTION OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
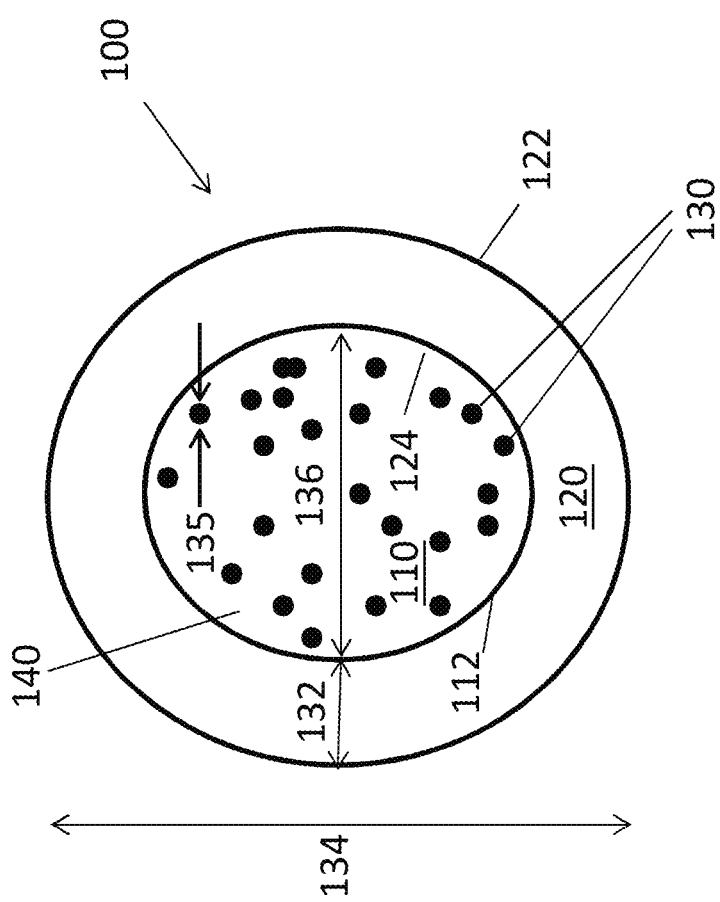
FIG. 1 is a schematic diagram of a magnetic microcarrier according to one embodiment.

Reference will now be made in greater detail to various embodiments of the subject matter of the present disclosure, some embodiments of which are illustrated in the accompanying drawings. The same reference numerals will be used throughout the drawings to refer to the same or similar parts.

A single, magnetic microcarrier bead 100 is shown schematically in cross-section in FIG. 1. Microcarrier bead 100 includes a composite core 110 and a coating 120 that completely surrounds and encapsulates the core. The composite core 110 comprises a unitary body defining an outer surface 112. The coating 120 is in direct physical contact with the outer surface 112 of the core 110 along an inner surface 124 of the coating 120.

The composite core is a mixture that comprises one or more particles 130 of a polycrystalline, inorganic magnetic material dispersed throughout a polymer matrix 140. The plurality of magnetic particles 130 may be homogeneously dispersed throughout the polymer matrix 140. Alternatively, the magnetic particles 130 may be segregated within the polymer matrix 140. The magnetic particles may have a particle size ranging from 200 nm to 500 micrometers, e.g., 0.2, 0.5, 1, 2, 5, 10, 20, 50, 100, 200 or 500 micrometers, including ranges between any of the foregoing.

The magnetic particles comprise a magnetic material that may be characterized as a soft magnetic material. As used herein, soft magnetic materials magnetize to saturation and experience a reversal in polarity in relatively weak magnetic fields at 25° C. In embodiments, the magnetic particles exhibit one or more of paramagnetism, superparamagnetism, ferromagnetism, superferromagnetism and ferrimagnetism. In embodiments, the magnetic particles exhibit superparamagnetism and superferromagnetism.

Individual domains within the magnetic particles may range in size from 0.5 nm to 500 nm, e.g., 0.5, 1, 2, 5, 10, 50, 100, 200 or 500 nm, including ranges between any of the foregoing. These small single crystal domains may be superparamagnetic. However, because the crystalline domains are packed tightly together, in embodiments they generate an interdomain magnetic interaction that is large enough to be measured, i.e., superferromagnetism.

The magnetic material may comprise a metal, metal alloy, or metal oxide, as well as combinations thereof. An example magnetic material is iron oxide ($Fe_3O_4$), though the magnetic particles may comprise a metal, metal alloy or metal oxide comprising one or more of B, Mg, Al, V, Cr, Mn, Fe, Co, Ni, Cu, Zn, Nb, Cd, Pr, Nd, Sm, Eu, Gd, Tb, Dy, Ho, Er, Tm and Yb. The magnetic particles may include one or more dopants, such as B, N, Al, Si or P. In one example, the magnetic material comprises iron oxide doped with boron or aluminum. Further example magnetic materials include cobalt oxides, nickel oxides, spinel compositions such as $CuFe_2O_4$, $NiFe_2O_4$, $MnFe_2O_4$, or $MgFe_2O_4$ and intermetallic compositions such as NiFe or NiCoFe.

The polymer matrix 130 within the core 110 comprises an indigestible or un-dissolvable polymer material or a mixture of such polymer materials, i.e., the polymer matrix is indigestible and/or not dissolvable under cell harvesting conditions. In embodiments, the polymer matrix within the core may comprise a digestible or dissolvable polymer material.

The polymer molecules within the core 110 may or may not be cross-linked. In embodiments, the polymer matrix comprises at least 90% by weight cross-linked polymer. The polymer molecules within the core may or may not be biodegradable. The polymer matrix encapsulates and inhibits aggregation of the magnetic particles. By way of example, the polymer matrix may comprise an organic polymer, a silica-based material, or biomaterials such as starch-based materials or hydrogels.

Suitable polymer matrix materials include polyethylene, polypropylene, and polystyrene. Example polymer matrix materials include poly(acrylic acid), polystyrene, polyaniline, poly(1,3-butadiene), poly(n-butyl methacrylate), poly(ε-caprolactone), poly(2-(dimethylamino)ethyl methacrylate, poly(dimethylsiloxane), polydivinylbenezene, polyethylene, poly(ethylene glycol), and poly(ethylene oxide), as well as co-polymers and mixtures thereof. Further example polymer matrix materials include calcium-alginate hydrogel, hyaluronic acid-poly-D-lysine based 3D gels, gelatin-poly(L-glutamic acid hydrogel glue), chitosan-glycerophosphate (CGP)-hydrogel, polyethylene glycol methacrylate 47 (PEGMA475), PEGMA950, methacrylic, and heparin gel. Also, because enzymes need not be used for cell harvesting, the polymer matrix material may be chosen to have one or more of the herein-disclosed properties and yet be degraded by enzymes. An example of such a material is Dextran, which is a complex, branched glucan (polysaccharide comprising plural glucose molecules).

The polymer matrix can be synthesized, for example, by emulsion polymerization, suspension polymerization and/or suspension cross-linking in conjunction with, for example, 3D printing, spray-drying, micro-fluidics-based droplet formation and/or lithographic processes, including chemical or photo lithography.

The coating that encapsulates the composite core comprises a polymer material or a mixture of polymer materials. In embodiments, the coating comprises a digestible or dissolvable polymer. In alternate embodiments, the coating comprises an indigestible or non-dissolvable polymer. The polymer molecules within the coating may or may not be cross-linked. In embodiments, the coating composition is covalently and/or ionically cross-linked. The cross-linking may be obtained, for example, by an ionotropic gelation method. Aspects of the coating composition, particularly with respect to embodiments comprising coatings that are digestible or dissolvable and which facilitate cell disattachment and cell harvesting are discussed below.

Trypsin, a protease, is frequently applied to cell culture surfaces to dissociate adhesive cells from the substratum once cultured cells reach confluence. For example, U.S. Pat. No. 4,994,388 discloses a method for culturing and harvesting anchorage-dependent cells employing microcarrier beads coated with collagen. Once cell growth is complete, the collagen is digested and the cultured cells are, in turn, separated from the insoluble microcarrier. Due to the proteolytic activity of trypsin, however, cell surface proteins are often non-selectively cleaved, which may lead to dysregulation of cell function. When trypsin is used to harvest cells, the cells typically require re-culture to recover cell surface receptors that are cleaved. It has been reported that trypsin is able to induce proteome alteration and cell physiological changes.

Further, treatment of cells with proteases such as trypsin removes antigens from cancer cells, which may render them unsuitable for the development of vaccines for anti-cancer therapies. Notably, trypsinization may release glycoproteins and sugars from the cell surface thereby leading to a loss of antigenic properties. In particular, trypsin treatment of SV40-transformed 3T3 cells may decrease their antigenicity in footpad assays. It has also been demonstrated that polyoma virus-transformed cells treated with trypsin failed to induce a delayed hypersensitivity reaction against tumor-specific antigens in footpad swelling assays.

Attempts to replace trypsin include the use of a non-proteolytic enzyme that digests polysaccharide beads. A proposed approach includes a microcarrier on which cells are grown and are subsequently separated from the microcarrier by enzymatically digesting the microcarrier. More specifically, chondrocytes were grown on dextran microcarrier beads and then the beads were digested using dextranase to separate the chondrocytes from the carrier.

According to several embodiments, a digestible or dissolvable coating that encapsulates the composite core can be prepared from at least an ionotropically cross-linked biopolymer selected, for example, from pectic acid (also known as polygalacturonic acid or PGA), partially-esterified pectic acid (also known as pectinic acid or PE PGA) or salts or mixtures thereof. A further example coating comprises alginic acid, also called algin or alginate. The gelation of these polyelectrolytes, e.g., alginate and pectate, results from the strong interactions between divalent cations, such as calcium, and blocks of either galacturonic or guluronic acid residues for alginate and PGA, respectively. The ionotropic gelation process is simple and inexpensive.

In embodiments, the coating may be prepared from a mixture of pectic acid or pectinic acid. Pectic acid can be formed by the hydrolysis of certain esters of pectins. Pectins are cell wall polysaccharides which have a structural role in plants. They are predominantly linear polymers based on a 1,4-linked alpha-D-galacturonate backbone, interrupted randomly by 1,2-linked L-rhamnose. The average molecular weight may be from about 50,000 to about 200,000 Daltons. Two major sources of pectins are, for example, from citrus peel (mostly lemon and lime) or apple peels, and can be obtained by extraction thereof.

The polygalacturonic acid chain of pectins can be partly esterified with methyl groups and the free acid groups may be partly or fully neutralized with monovalent ions such as sodium, potassium, or ammonium ions. Polygalacturonic acids partly esterified with methanol are called pectinic acids, and salts thereof are called pectinates.

The degree of methylation (DM) for high methoxyl (HM) pectins typically can be, for example, from 60 to 75 mol % and that for low methoxyl (LM) pectins can be from 1 to 40 mol %, e.g., 10 to 40 mol % or 20 to 40 mol %, including intermediate values and ranges.

Coatings can be prepared from the LM pectins, for example from polygalacturonic acid containing less than 20 mol % methoxyl groups. In embodiments, the polygalacturonic acid has no or negligible methyl ester content as pectic acids. For simplicity both pectinic acid having no or only negligible methyl ester and low methoxyl (LM) pectins are referred to as PGA in the disclosure.

In embodiments, some chemical cross-linking can be performed but the level of chemical crosslinking, being irreversible, should be sufficiently low, for example, less than about 10 to 20 mol %, in embodiments where digestion of the coating, e.g., by pectinase, is desired. It is known that the structure of the gel can significantly influence degradation where, for example, a more highly cross-linked gel can lead to overall longer degradation times. Crosslinking reduces pore size of the hydrogel and restricts enzyme access, and consequently reduces the digestion efficiency. Crosslinking can be performed by ionotropic gelation or by internal gelation. Ionotropic gelation is based on the ability of polyelectrolytes to cross link in the presence of multivalent counter ions to form cross-linked hydrogels.

When partially-esterified pectic acid is selected, the degree of esterification can be, for example, about 40 mol % or less, such 1, 2, 4, 10, 20 or 40 mol %, including ranges between any of the foregoing.

PGA or alginate-coated beads, due to their hydrogel nature and negative charge, do not readily support cell attachment without specific treatment. The polymer-coated beads can be functionalized with moieties promoting cell adhesion, for example, with peptides. Peptides containing amino acid sequences potentially recognized by proteins from the integrin family, or leading to an interaction with cellular molecules able to sustain cell adhesion, are candidates for functionalizing the present magnetic microcarriers. Example peptides include, for example, bone sialoprotein peptides (BSP), vitronectin, fibronectin, laminin, collagen, and like peptides, and mixtures thereof.

In embodiments, the coating composition comprises a peptide-polymer conjugate, which promotes the attachment of anchorage dependent cells. By way of example, the peptide-polymer conjugate is poly(meth)acrylate or poly (meth)acrylamide copolymer comprising an adhesion peptide. The peptide-polymer conjugate may be Synthemax®-SC.

The magnetic microcarrier of the disclosure can be, if desired, functionalized by simple physical adsorption of polymers such as adhesive peptides. Suitable polymers promoting cell adhesion comprise synthetic polymers. Eliminating chemical derivatization from the manufacturing process by using physical adsorption of an adhesion promoting polymer appears attractive since chemical derivatization is time consuming, labor intensive, requires a large amount of reagents, and generates a large amount of waste chemicals.

A surface layer prepared from polymers comprising adhesive peptides is particularly effective when applied to magnetic beads that have coatings cross-linked by internal gelation, and, in contrast, fails on coatings cross-linked by external gelation.

Without being bound by theory it is believed that the surface compactness of externally formed gels offers a higher resistance to diffusion of the peptide polymer used for coating in contrast to the better absorption/adsorption of the peptide polymer on porous and more homogeneous gel formed by internal gelation. It is believed that a more stable adsorption of the peptide polymer is achieved and results in a more efficient cell attachment and better cell growth.

In embodiments, the coating may comprise one or more functional groups that are incorporated onto the bead surface. Example functional groups include carboxylate groups, amino groups, methyl groups, methylene groups, thiol groups, anhydride groups, phosphoric acid groups, sulfuric acid groups, or phosphatide groups. These surface modifications can enable various characteristics, such as promoting cell attachment, enabling serum-free cell growth, or enabling cell detachment, e.g., without enzyme (protease) treatment.

Additional surface-modifying materials, which can enhance cell attachment and growth, include extracellular matrix, extracellular matrix mimics, Matrigel® matrix, collagen, fibronectin, laminin, Synthemax®-SC, Puramatrix™, vitronectin, and osteopontin.

In the resulting magnetic beads, the optionally surface-functionalized polymer coating may comprise from about 2 to 40 wt. % of the total mass of the beads. For instance, the coating may comprise 2, 5, 10, 15, 20, 25, 30, 35 or 40 wt. % of the total bead mass, including ranges between any of the foregoing. Thus, the core may comprise 60 to 98 wt. % of the total mass of the beads.

As illustrated in FIG. 1, the core 110 has a particle size 136, the magnetic particles have a particle size 135, and the magnetic bead 100 has a particle size 134. The term "particle size" is used to describe the maximum linear dimension of a given component. In the case of a spherical particle, the particle size is the diameter. In the case of an oblong particle, the particle size is the "length" of the particle. An example average particle size for a plurality of magnetic beads 100 may range from about 1 micrometer to 1000 micrometers, e.g., 1, 2, 5, 10, 20, 50, 100, 200, 500 or 1000 micrometers, and may be defined for a given material batch over a range of any two of the aforementioned values. For cell culture, the size of the microcarrier bead is preferably greater than the size of a single cell, which is typically greater than 10 micrometers for most anchorage-dependent cells.

In embodiments, the particle size of the core ranges from about 500 nm to 950 microns, e.g., 0.5, 1, 2, 5, 10, 20, 50, 100, 200, 500 or 950 microns, including ranges between any two of the foregoing. The coating 120 has a thickness 132 defined as the average shortest distance between the inner surface 124 of the coating and the outer surface 122 of the coating. In embodiments, the coating may have a substantially uniform thickness or a variable thickness depending, for example, on the method used to form the coating. An example average thickness for the coating 120 may range from about 10 nm to 1000 nm, e.g., 10, 20, 50, 100, 200, 500 or 1000 nm, including ranges between any two of the foregoing. In embodiments, a portion of the core and/or a portion of one or more magnetic particles embedded within the core may be exposed at the outer surface of the microcarrier bead.

In some embodiments, the magnetic microcarrier beads 100 may be substantially spherically shaped. However, other shapes are contemplated herein, such as, but not limited to asymmetric shapes or spheroids, including disks, rods, etc. In embodiments, the disclosed magnetic beads have a density of 1 to 1.2 $g/cm^3$, e.g., 1.0, 1.05, 1.1, 1.15 or 1.2 $g/cm^3$. In embodiments, the magnetic particles have a surface area of at least 10 $m^2/g$, e.g., 10-20 $m^2/g$.

As a result of the core properties, the microcarrier beads exhibit low (e.g., non-zero) coercivity (e.g., less than 300 Oe) and high magnetization (e.g., at least 50 emu/g) (i.e., a "soft" magnetic material). By way of example, the coercivity of the microcarrier beads may be 10, 20, 50, 100, 150, 200, 250 or 300 Oe, including ranges between any of the foregoing. The magnetization of the microcarrier beads may be, for example, 50, 55, 60, 65, 70, 75, 80, 85, 90, 95 or 100 emu/g, including ranges between any of the foregoing.

A sample comprising the magnetic microcarriers can be stirred via the application of a magnetic field, which creates less hydrodynamic stress than impellers and results in less damage to cells located on the surface of the beads. In embodiments, cells grow and expand on the surface of the microcarriers using regular media, chemically defined media, or serum free media. The magnetic properties of the microcarriers enable the agitation of microcarriers with magnetic force.

In use, the high magnetization of the microcarrier beads promotes a rapid magnetic response and high magnetic separation efficiency. The high binding capacity of the microcarrier beads enables a more efficient and economic materials utilization, whereby a greater number of samples can be processed within a given container volume per assay. The magnetic bead material can be used to bind biomolecules and separate the bound biomolecule by magnetic force. The bound molecules can then be reversibly released, i.e., through use of an appropriate buffer.

In embodiments, the microcarrier enables rapid and complete cell harvesting by contacting the microcarrier, on which the cells were grown, with pectinase, and optionally a chelating agent, e.g., EDTA, and without the need of adding any protease.

In embodiments, the disclosure provides a method for harvesting cultured cells, comprising culturing cells on the surface of the microcarrier beads, disassociating the cells from the surface, and separating the dissociated cells from the magnetic beads using magnetic force.

In the case of harvesting conditioned media, the microcarriers can be directly separated from the media using magnetic force.

In embodiments, the disclosure provides a method for preparing conditioned media, comprising culturing cells on the surface of the microcarrier beads to form conditioned media, and separating the conditioned media from the magnetic beads (and the cultured cells) using magnetic force.

In each of the foregoing embodiments, magnetic field-based agitation may accompany the cell culture.

The magnetic particles disclosed herein may be used in bioprocessing, such as for the separation, isolation and/or purification of cells, cell components, or cellular products, including antibodies, viruses, proteins, drugs, etc. By way of example, the magnetic particles may be used for the separation, isolation and/or purification of endosomes, membrane fractions, mitochondria, ribosomes, sub cellular organelles, etc.

As a further example, the magnetic particles may be used for the purification of nucleic acids, including cell-free fetal DNA, PCR product DNA, genomic DNA, mRNA, total RNA, microRNA, viral RNA or DNA, bacterial RNA or DNA, plasmid DNA, etc. Nucleic acids, as well as peptides and proteins, may be derived from a variety of biological sources, such as whole blood, plasma, serum, buffy coat, bone marrow, amniotic fluid, spinal fluid, other bodily fluids (e.g., saliva, nasal, cheek, vaginal or throat swabs), hair follicles, stool, urine, tissue, fresh or frozen samples, formalin-fixed paraffin-embedded (FFPE) samples, and plant samples.

Nucleic acids purified with particulate magnetic material can be used for various applications, such as (non-invasive) prenatal screening, cancer testing, virus or bacteria detection/diagnostics, blood donor screening, organ donor matching, genetic disease studies for inherited disorders, genealogical testing, ethnicity testing, human leukemia antigen (HLA) testing, agriculture, or genetic/genomic/epigenomic research. Peptides or proteins adsorbed to the surface of a magnetic particle may be used as targeting molecules for ELISA or chemiluminescence assays.

The disclosed microcarriers enable effective cell growth, and can be tailored with different surface modifications for different cell types and/or various cell culture conditions. The magnetic properties of the microcarriers enable magnetic field-induced agitation and easy separation for harvesting cells or purifying conditioned media, which reduces damage caused by conventional physical (impeller-based) approaches. The digestible surface coating enables cell release and harvesting of the cultured cells without using an enzyme treatment.

Figure 2:
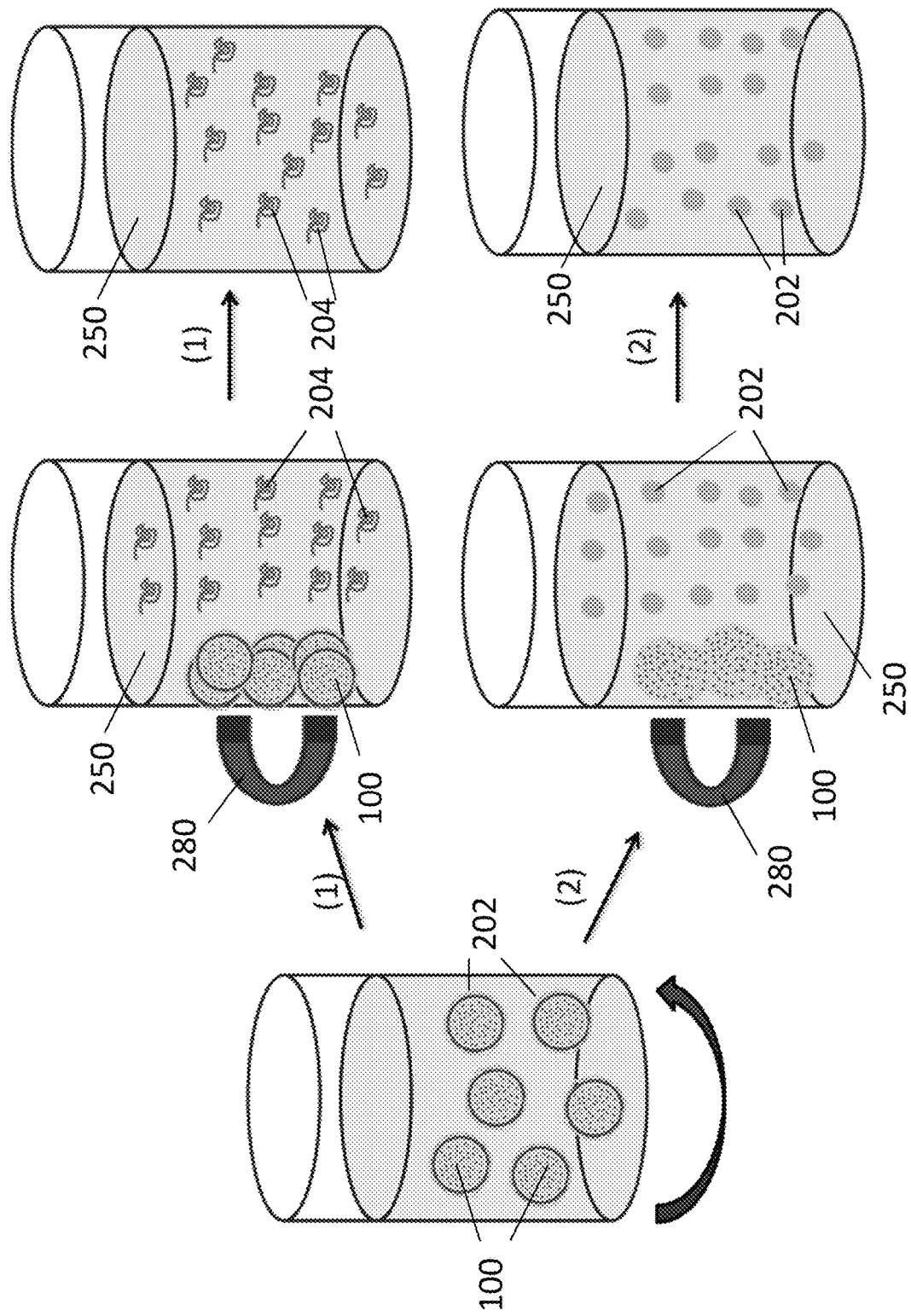
FIG. 2 illustrates exemplary bioprocessing methods utilizing magnetic microcarriers.

With reference to FIG. 2, illustrated are example processes using the disclosed magnetic microcarrier beads 100. During cell culture, magnetic microcarriers with surface-attached cells 202 can be agitated (e.g., stirred) using a magnetic field. Once cell culture reaches a desires state, either (1) conditioned media (i.e., media 250 comprising biomolecules 204), (2) cells 202, or both can be harvested.

In process route (1), biomolecules 204 produced by cells 202 are the desired product. Example biomolecules include peptides, proteins, lipids, nucleic acids and polysaccharides. In the corresponding separation or purification step, microcarrier beads 100 attached with the parent cells 202 can be extracted by a magnet 280 and separated from the conditioned media 250 enabling collection of the conditioned media. In process route (2), cells 202 that have expanded on the microcarrier beads 100 can be detached from the microcarrier bead surface with or without enzyme treatment depending on the surface modification. The remaining indigestible microcarrier bead cores can then be separated from the media using a magnet 280 and the cells 202 can be collected. If both biomolecules and cells are sought, biomolecules can be collected first following route (1) and then cells can be collected following route (2).

In certain embodiments, the magnetic core, after digestion to remove the coating, can be directly used as a separation matrix to purify nucleic acid materials, proteins, or cell populations from the cell culture media. For instance, a magnetic core having a binding agent such as net surface charge or an antibody can be used to bind to specific proteins or cell populations having a specific cell surface protein that the binding agent recognizes. The microcarrier composite core having the nucleic acid materials, proteins, or cell population can be separated from the media using magnetic force. With increasing exploration of genetically-modified cell therapy (e.g., stem cells, or T cells) has come the need to purify specific cell populations from a mixture of cell populations. These purifications generally use antibodies specifically recognizing certain cell surface proteins.

In an example embodiment, a method for isolating a target such as nucleic acid materials, proteins, or cell populations comprises culturing cells on a surface of the magnetic bead of claim 1, wherein a surface of the composite core comprise a binding agent, and dissolving the coating to disassociate the cells from the composite core.

Disclosed is a cell culture article, such as a substrate having a chemically-modified surface, and methods of making and using the article. The cell culture article enables cell culture in a chemically-defined medium or serum-free medium, and allows for the harvest of cultured cells without using any protease.

As used herein, the singular forms "a," "an" and "the" include plural referents unless the context clearly dictates otherwise. Thus, for example, reference to a "magnetic microcarrier bead" includes examples having two or more such "magnetic microcarrier beads" unless the context clearly indicates otherwise.

The term "include" or "includes" means encompassing but not limited to, that is, inclusive and not exclusive.

"Optional" or "optionally" means that the subsequently described event, circumstance, or component, can or cannot occur, and that the description includes instances where the event, circumstance, or component, occurs and instances where it does not.

Ranges can be expressed herein as from "about" one particular value, and/or to "about" another particular value. When such a range is expressed, examples include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. Any recited single or multiple feature or aspect in any one claim can be combined or permuted with any other recited feature or aspect in any other claim or claims.

It is also noted that recitations herein refer to a component being "configured" or "adapted to" function in a particular way. In this respect, such a component is "configured" or "adapted to" embody a particular property, or function in a particular manner, where such recitations are structural recitations as opposed to recitations of intended use. More specifically, the references herein to the manner in which a component is "configured" or "adapted to" denotes an existing physical condition of the component and, as such, is to be taken as a definite recitation of the structural characteristics of the component.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a magnetic particle comprising a composite core and a coating include embodiments where a magnetic particle consists of a composite core and a coating, and embodiments where a magnetic particle consists essentially of a composite core and a coating.

It will be apparent to those skilled in the art that various modifications and variations can be made to the present inventive technology without departing from the spirit and scope of the disclosure. Since modifications, combinations, sub-combinations and variations of the disclosed embodiments incorporating the spirit and substance of the inventive technology may occur to persons skilled in the art, the inventive technology should be construed to include everything within the scope of the appended claims and their equivalents.

We claim:

1. A magnetic bead comprising a composite core and a coating that surrounds and encapsulates the composite core, wherein:
   the composite core comprises magnetic particles having a particle size of 200 nm to 500 micrometers homogenously dispersed throughout a cross-linked polymer matrix to form a unitary body, wherein the polymer matrix is not dissolvable under cell harvesting conditions;
   the coating comprises a polymer which is at least one of pectic acid, partially-esterified pectic acid, alginic acid, and salts thereof, wherein the polymer is functionalized for cell adhesion;
   the coating has an average thickness of 10 nm to 500 nm; and
   the diameter of the magnetic bead is in the range of 1 micrometer to 1000 micrometers.

2. The magnetic bead of claim 1, wherein the magnetic particles comprise a metal, metal alloy or metal oxide comprising one or more of B, Mg, Al, V, Cr, Mn, Fe, Co, Ni, Cu, Zn, Nb, Cd, Pr, Nd, Sm, Eu, Gd, Tb, Dy, Ho, Er, Tm and Yb.

3. The magnetic bead of claim 1, wherein the magnetic particles comprise iron oxide.

4. The magnetic bead of claim 1, wherein the polymer matrix comprises a polymer selected from the group consisting of poly(acrylic acid), polystyrene, polyaniline, poly(1,3-butadiene), poly(n-butyl methacrylate), poly($\varepsilon$-caprolactone), poly(2-dimethylamino)ethyl methacrylate, poly(dimethylsiloxane), polydivinylbenezene, polyethylene, poly(ethylene glycol), and poly(ethylene oxide).

5. The magnetic bead of claim 1, wherein the diameter of the composite core is in the range of 400 nm to 950 microns.

6. The magnetic bead of claim 1, wherein the composite core comprises at least 60 wt % of the bead.

7. The magnetic bead of claim 1, wherein the composite core further comprises a binding agent on a surface thereof.

8. The magnetic bead of claim 1, wherein the coating further comprises a peptide-polymer conjugate.

9. The magnetic bead of claim 1, wherein the coating further comprises adhesive peptides.

10. The magnetic bead of claim 1, further comprising surface-attached cells.

11. A method for preparing conditioned media, comprising:
    culturing cells on the surface of the magnetic bead of claim 1 to form conditioned media; and
    separating the conditioned media from the magnetic bead using magnetic force.

12. The method of claim 11, wherein the culturing comprises agitating the magnetic bead by applying a magnetic force to the magnetic bead.

13. A method for harvesting cultured cells, comprising:
    culturing cells on the surface of the magnetic bead of claim 1;
    disassociating the cells from the surface; and
    separating the dissociated cells from the magnetic beads using magnetic force.

14. The method of claim 13, wherein the disassociating is accomplished free of a protease.

15. A method for isolating a target, comprising:
    culturing cells on a surface of the magnetic bead of claim 1, wherein a surface of the composite core comprises a binding agent for the target; and
    dissolving the coating to disassociate the cells from the composite core and allow the target to bind the binding agent.

16. The method of claim 15, wherein the binding agent comprises a positive or negative charge.

17. The method of claim 15, wherein the binding agent comprises an antibody.

18. The method of claim 15, wherein the target is selected from the group consisting of nucleic acid materials, proteins and cell populations.

* * * * *